(12) United States Patent
Hoke et al.

(10) Patent No.: US 9,863,877 B2
(45) Date of Patent: Jan. 9, 2018

(54) INFRARED SPECTROMETER AND SCANNER UTILIZING ATTENUATED TOTAL REFLECTION

(71) Applicant: Agilent Technologies, Inc., Santa Clara, CA (US)

(72) Inventors: Charles Hoke, Menlo Park, CA (US); Christopher Ryan Moon, Los Gatos, CA (US); Andrew Ghetler, San Jose, CA (US); Yuri Beregovski, San Jose, CA (US); Richard P. Tella, Sunnyvale, CA (US); Yang Han, Sunnyvale, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 122 days.

(21) Appl. No.: 14/863,341

(22) Filed: Sep. 23, 2015

(65) Prior Publication Data
US 2017/0082538 A1 Mar. 23, 2017

(51) Int. Cl.
*G01N 21/552* (2014.01)
*G01N 21/35* (2014.01)
(Continued)

(52) U.S. Cl.
CPC .......... *G01N 21/552* (2013.01); *G01J 3/0213* (2013.01); *G01J 3/0229* (2013.01);
(Continued)

(58) Field of Classification Search
CPC .............. G02B 17/006; G02B 17/0808; G02B 17/0856; G02B 17/086; G02B 17/004;
(Continued)

(56) References Cited

U.S. PATENT DOCUMENTS 5,093,580 A * 3/1992 Sting .................. G01N 21/4738
250/216
5,200,609 A * 4/1993 Sting .................... G01N 21/552
250/226
(Continued)

FOREIGN PATENT DOCUMENTS

JP        09304271 A    11/1997
WO   WO 2016/110935 A1 * 7/2016 ........... G01N 21/552

OTHER PUBLICATIONS

GB Search Report dated Feb. 24, 2017, Application No. GB1615877.6.

*Primary Examiner* — Gordon J Stock, Jr.

(57) ABSTRACT

A scanner and an attenuated total reflection (ATR) objective for use in such scanners are disclosed. The ATR objective includes first and second optical elements and an input port. The input port receives an input collimated light beam that is focused to a point on a planar face of the first optical element by the second optical element such that substantially all of that portion is reflected by the planar face and no portion of the input beam strikes the planar face at an angle less than the critical angle. The second optical element also generates an output collimated light beam from light reflected from the planar thce that is characterized by a central ray that is coincident with the central ray of the input collimated light beam. A light beam converter receives the first collimated light beam and generates the input collimated light beam therefrom.

17 Claims, 10 Drawing Sheets

(51) Int. Cl.
*G02B 13/14* (2006.01)
*G02B 17/00* (2006.01)
*G02B 17/08* (2006.01)
*G01N 21/3563* (2014.01)
*G01N 21/39* (2006.01)
*G01J 3/02* (2006.01)

(52) U.S. Cl.
CPC .............. *G01N 21/35* (2013.01); *G02B 13/14* (2013.01); *G02B 17/006* (2013.01); *G02B 17/0808* (2013.01); *G01N 21/3563* (2013.01); *G01N 2021/399* (2013.01); *G01N 2201/0633* (2013.01); *G01N 2201/10* (2013.01); *G01N 2201/101* (2013.01)

(58) Field of Classification Search
CPC ...... G02B 17/061; G02B 13/14; G01N 21/35; G01N 21/3504; G01N 21/3563; G01N 21/3577; G01N 21/3581; G01N 21/359; G01N 21/552; G01N 2021/3568; G01N 2021/3572; G01N 2021/399; G01N 2201/0633; G01N 2201/101; G01N 2201/10; G01J 3/108; G01J 3/0213; G01J 3/0229

USPC ....... 356/300, 302, 303, 310, 319, 320, 326, 356/445; 250/338.1, 339.01, 339.06, 250/339.07
See application file for complete search history.

(56) References Cited

U.S. PATENT DOCUMENTS

| | | | |
|---|---|---|---|
| 5,347,364 A * | 9/1994 | Kawasaki | G01N 21/552 250/341.1 |
| 5,729,018 A * | 3/1998 | Wells | G02B 21/04 250/339.07 |
| 7,492,460 B2 * | 2/2009 | Koshoubu | G01J 3/02 356/445 |
| 8,873,140 B2 * | 10/2014 | Juette | G01N 21/552 359/350 |
| 9,291,556 B2 * | 3/2016 | Nakagawa | G01N 21/552 |
| 2017/0082490 A1 * | 3/2017 | Hoke | G01J 3/0224 |

* cited by examiner

INFRARED SPECTROMETER AND SCANNER UTILIZING ATTENUATED TOTAL REFLECTION

BACKGROUND

Quantum cascade lasers provide a tunable mid-infrared (MIR) light source that can be used for spectroscopic measurements and images. Many chemical components of interest have molecular vibrations that are excited in the MIR region of the optical spectrum, which spans wavelengths between 5 to 25 microns. Hence, measuring the absorption of MIR light at various locations on a sample can provide useful information about the chemistry of the sample as a function of position on the sample.

One class of imaging spectrometers measures the light directly reflected from the sample as a function of position on the sample and wavelength of the illuminating MIR light. The amount of light that is reflected depends on both the chemical and physical attributes of the sample. Hence, comparing spectra generated with direct reflection to absorption with known chemical absorption spectra that are available in libraries presents significant challengers.

SUMMARY

The present invention includes a scanner and an attenuated total reflection (ATR) objective for use in such scanners. The scanner includes a light source that generates a first collimated light beam and an ATR objective. The ATR objective includes first and second optical elements and an input port. The first optical element includes a planar face, characterized by a critical angle. The input port is adapted to receive a first input collimated light beam characterized by a central ray, the input port being characterized by a pivot point through which the central ray passes and an orientation direction that passes through the pivot point. The second optical element focuses a portion of the first input collimated light beam to a point on the planar surface such that substantially all of that portion is reflected by the planar face and no portion of the input beam strikes the planar face at an angle less than the critical angle. The second optical element generates a first output collimated light beam from light reflected. from the planar face. The first output optical beam is characterized by a central ray that is coincident with the central ray of the first input collimated light beam. A first detector measures an intensity of light in the first output collimated light beam. The scanner also includes a light beam converter that receives the first collimated light beam and generates the first input collimated light beam therefrom in response to an orientation signal that determines an orientation between the orientation direction and the central ray of the input collimated light beam.

In one aspect of the invention, the scanner includes a controller that generates the orientation signal and causes the light beam converter to sequence through a predetermined set of different orientations between the orientation direction and the central ray of the input collimated light beam.

In one aspect of the invention, the light beam converter includes first and second parabolic reflectors and a beam deflector. The beam deflector receives the first collimated light beam and deflects that light beam to a point on the first parabolic reflector, the point being determined by the orientation signal. The second parabolic reflector is positioned to receive light reflected from the first parabolic reflector and collimate the received light to generate the first input collimated light beam.

In another aspect of the invention, the scanner also includes a reflective objective having an input port, an optical element, and a third parabolic reflector. The input port is configured to receive a second input collimated light beam characterized by a central ray. The optical element focuses the second input collimated light beam to a spot at a predetermined point. The optical element receives light reflected from the predetermined point and forms a second output collimated beam therefrom. The second output collimated beam is characterized by a central ray that is coincident with the central ray of the second input collimated light beam. The third parabolic mirror intercepts light reflected from the first parabolic mirror and generates the second input collimated light beam therefrom when the third parabolic minor is in a first position. The third parabolic mirror does not intercept light from the first parabolic mirror when the third parabolic mirror is in a second position. The position of the parabolic material is determined by an actuator that is responsive to a mode signal.

In another aspect of the invention, the scanner also includes an actuator that moves the reflective objective in relationship to a specimen stage such that the spot moves in a line parallel to the stage. The controller causes the beam deflector to move the point on the first parabolic reflector such that the spot moves in a direction orthogonal to the line.

In another aspect of the invention, the scanner includes a second detector that measures an intensity of light in the first collimated light beam.

An ATR objective according to the present invention includes first and second optical elements, an input port and a mask. The first optical element includes a planar face. The input port is adapted to receive a collimated beam of light characterized by a central ray, the input port being characterized by a pivot point through which the central ray passes. The mask divides the collimated beam of light into first and second portions, the mask preventing light in the first portion from reaching the planar face. The second optical element focuses the second portion on a point on the planar face such that substantially all of the second portion is reflected from the planar face, the second optical element collecting light reflected from the planar face and collimating the collected light into an output beam that leaves the input port in a collimated beam having a central ray coincident with the central ray of the input collimated light beam.

In one aspect of the invention, the mask absorbs light in the first portion.

In another aspect of the invention, the first optical element is transparent to light having a wavelength between 3 and 20 microns. In another aspect, the first optical element is transparent to light having a wavelength between 5 and 12.5 microns.

In another aspect of the invention, the first optical element includes a crystalline material, and the planar face is a facet of a crystal of the crystalline material.

In another aspect of the invention, the first optical element includes a glass that is transparent to light having a wavelength between 3 and 20 microns. In another aspect, the first optical element is a glass that is transparent to light having a wavelength between 5 and 12.5 microns.

In another aspect of the invention, the second optical element is a refractive element. In another aspect, the second optical element is a reflective element.

In another aspect of the invention, the input port is characterized by a direction that passes through the pivot point and wherein the point on the planar face depends on an orientation of the central ray of the collimated beam relative to the direction.

DETAILED DESCRIPTION

Figure 1:
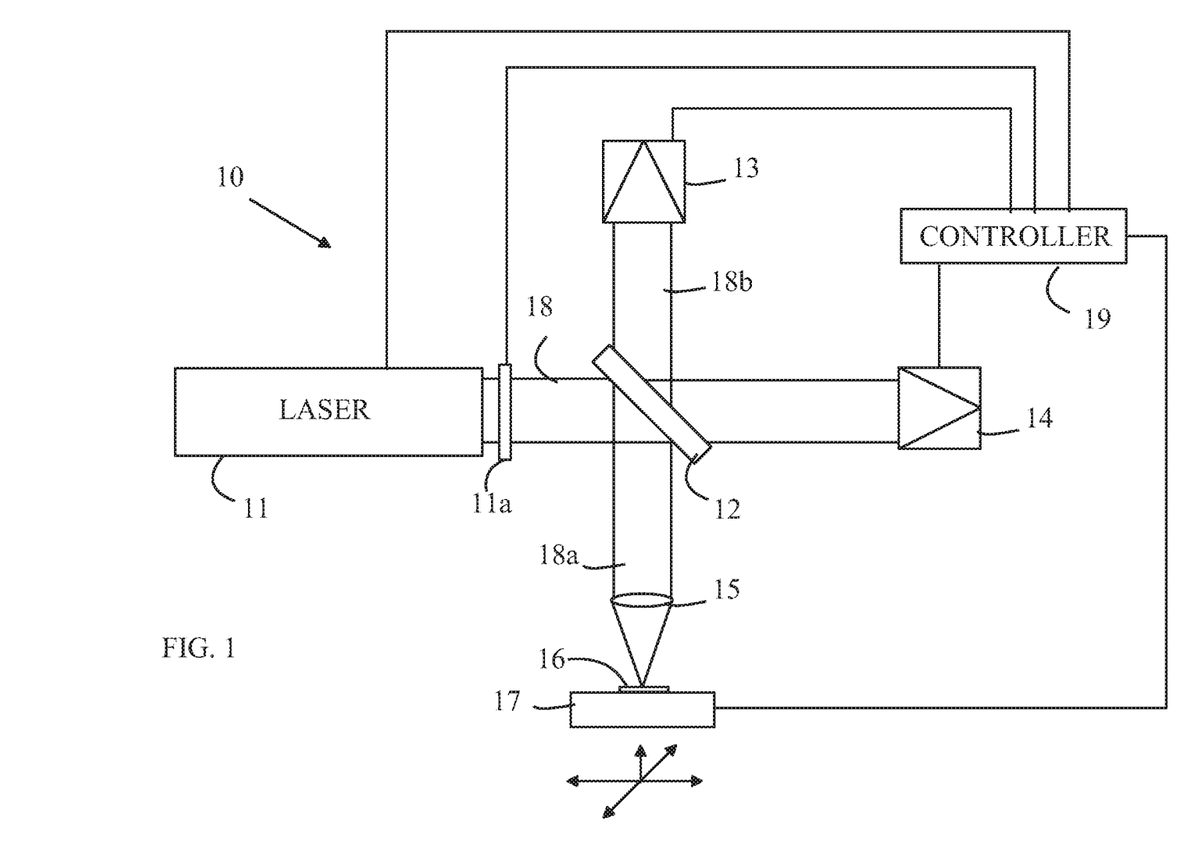
FIG. 1 illustrates one embodiment of a direct MIR imaging system.

The manner in which the present invention provides its advantages can be more easily understood with reference to FIG. 1 which illustrates one embodiment of a direct MIR imaging system. Imaging system 10 includes a quantum cascade laser 11 that generates a collimated light beam 18 having a narrow band of wavelengths in the MIR. In one aspect of the invention, quantum cascade laser 11 is a quantum cascade laser having a tunable wavelength that is under the control of controller 19. The intensity of light from quantum cascade laser 11 is controlled by a variable attenuator 11a that is also under the control of controller 19. Collimated light beam 18 is split into two beams by a partially reflecting mirror 12. Light beam 18a is directed to a lens 15 that focuses that beam onto a specimen 16 that is mounted on xyz-stage 17 that can position specimen 16 relative to the focal point of lens 15. Light that is reflected back from specimen 16 is collimated into a second beam that has a diameter determined by the aperture of lens 15 and returns to partially reflecting mirror 12 along the same path as light beam 18a. While the first and second beams are shown as having the same cross-section in FIG. 1, it is to be understood that the second beam could have a different cross-section than the first beam. A portion of the second beam is transmitted through partially reflecting mirror 12 and impinges on a first light detector 13 as shown at 18b. Light detector 13 generates a signal related to the intensity of light in beam 18b. Controller 19 computes an image as a function of position on specimen 16 by moving specimen 16 relative to the focal point of lens 15 using xyz-stage 17.

Controller 19 also monitors the beam intensity of the light in collimated light beam 18 using a second light detector 14 that receives a portion of the light generated by quantum cascade laser 11 through partially reflecting mirror 12. Quantum cascade laser 11 is typically a pulsed source. The intensity of light from pulse to pulse can vary significantly, and hence, the pixels of the image are corrected for the variation in intensity by dividing the intensity measured by light detector 13 by the intensity measured by light detector 14. In addition, since the light intensity from quantum cascade laser 11 is zero between pulses, controller 19 only sums the ratio of intensities from light detectors 13 and 14 during those times at which the output of light detector 14 is greater than some predetermined threshold. This aspect of the present invention improves the signal-to-noise ratio of the resultant image, since measurements between pulses contribute only noise, which is removed by not using measurements between pulses.

Ideally, the input wavelength could be varied over an appropriate range of wavelengths and the light absorbed by the sample determined from the reflected light signal. That absorption spectrum could then be compared to standard absorption spectra from a library to provide information about the chemical composition of the sample at the point being illuminated. The difference in light intensity between the input beam that strikes the specimen and the light that is reflected from the specimen depends on the light that is absorbed by the specimen. Unfortunately, part of the light striking the sample is scattered. A significant fraction of the scattered light does not reach light detector 13. The scattered light depends on the surface properties of the specimen. For example, a specimen having crystals embedded in its surface will specularly reflect the incoming light in a direction that depends on the angles of the crystal facets with respect to the incoming light. To compare the light losses as a function of wavelength with standard libraries, the contribution of the scattered light must be known or an arrangement in which the scattered light intensity is minimal must be used.

Figure 2:
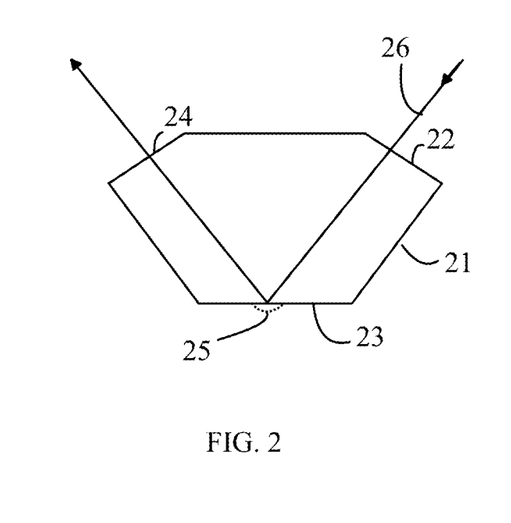
FIG. 2 is a cross-sectional view of an interface crystal that can facilitate the measurement of the absorption of light by a sample in the reflective geometry mode.

One type of reflection spectroscopy that does not suffer from the problems associated with scattered light is referred to as ATR spectroscopy. ATR functions can be more easily understood with reference to FIG. 2, which is a cross-sectional view of an interface crystal that can facilitate the measurement of the absorption of light by a sample in the reflective geometry mode. Crystal 21 has a high index of refraction. Light beam 26 enters crystal 21 thorough port 22 and strikes facet 23 at an angle that is greater than the critical angle. The light beam is totally reflected from facet 23 and exits the crystal through port 24. At the point at which the light beam is reflected from facet 23, the electric field associated with the light beam extends outside the crystal as shown at 25. If the medium under facet 23 absorbs light at the wavelength of light beam 26, the evanescent field will interact with the medium and energy will be transferred from the light beam to the medium. In this case, the energy in the beam leaving crystal 21 will be reduced. The difference in intensity between the input and output beams as a function of wavelength is a spectrum that matches a high-quality transmission spectrum and can easily be used for matching conventional spectra for various chemical compounds.

While an interface crystal of the type discussed above is useful in measuring a MIR spectrum of a point on a sample, it presents challenges if an image of an area on the specimen is needed, particularly if the surface of the specimen is not smooth. To form an image, the interface must be moved relative to the specimen. To prevent the interface crystal from damaging the specimen, the specimen must be moved vertically to allow the crystal to be located at the next point of interest. The time for such point to point measurements makes a combination imaging and spectrometer instrument impractical unless very long times are available to generate a spectrum at each point on a specimen in high resolution.

Figure 3A:
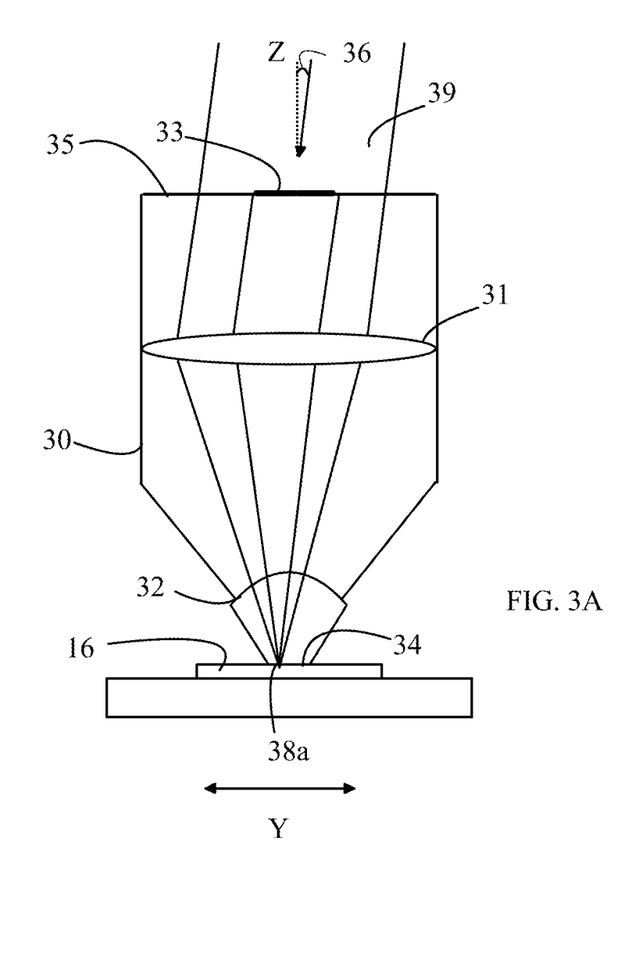
FIGS. 3A-3D illustrate a scanning ATR objective for a MIR microscope.
Figure 3B:
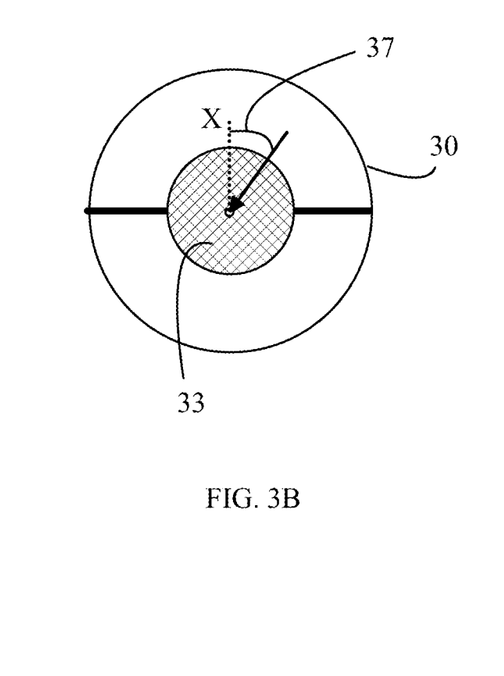

The present invention reduces the scanning time for ATR measurements by utilizing an ATR objective and a scanning MIR beam that allows small areas on the sample to be measured in ATR mode without moving the ATR objective of the specimen stage. Refer now to FIGS. 3A-3D, which illustrate a scanning ATR objective for a MIR microscope. Refer first to FIGS. 3A and 3B. FIG. 3A is a cross-sectional view through an ATR objective 30, and FIG. 3B is a top view of ATR objective 30 as "seen" by a collimated light beam 39 entering ATR objective 30 at a non-normal angle to the top surface of ATR objective 30. ATR objective 30 includes a crystal 32 having a high index of refraction for light in the MIR. Crystal 32 has a facet 34 that is parallel to the plane of specimen 16. ATR objective 30 includes an optical component 31 which focuses the collimated light onto facet 34. A beam blocker 33 prevents light from the center of collimated light beam 39 from striking facet 34 at an angle less than the critical angle, and hence, entering specimen 16. The light reflected from facet 34 is collimated by optical component 31 and leaves ATR objective 30 along the same beam path as collimated light beam 39. When light reflects from facet 34, the evanescent field extends into the specimen. The energy absorbed by specimen 16 reduces the intensity of the light reflected from facet 34.

The details of the optical system that directs light into ATR objective 30 will be discussed in more detail below. For the purposes of the present discussion, it is sufficient to note that the position of spot 38a is determined by the angles at which the collimated light beam 39 enters port 35. The direction of collimated light beam 39 relative to ATR objective 30 can be specified by the two angles shown at 36 and 37. Consider the XYZ coordinate system shown in the figure. Angle 36 is the angle between the normal to port 35 and the direction of collimated light beam 39. Angle 37 is the angle between the x-axis and the projection of the direction of collimated light beam 39 on the xy plane. By changing these two angles, the point at which the light beam is focused on facet 34 can be varied.

Figure 3C:
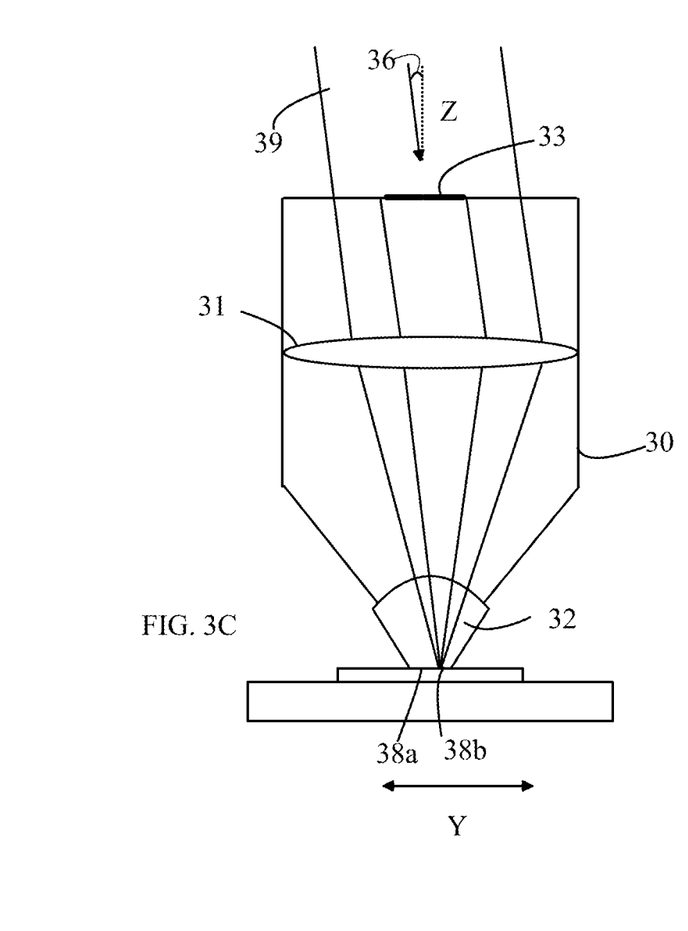
Figure 3D:
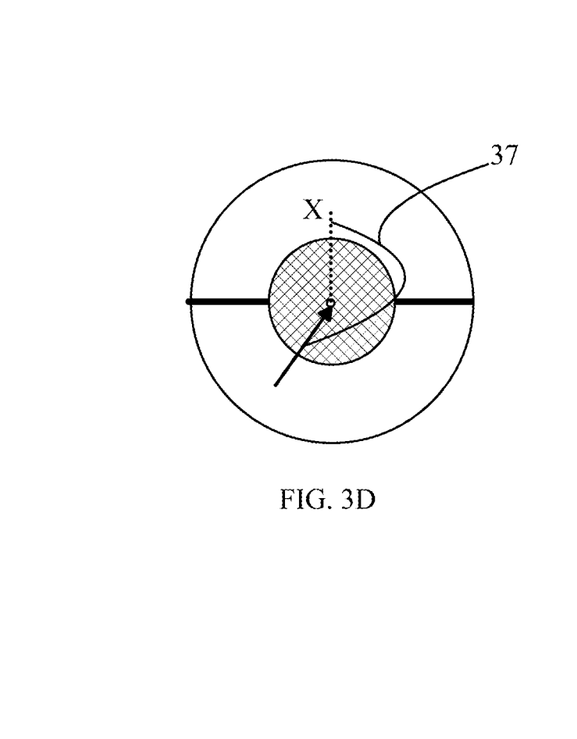

Refer now to FIGS. 3C-3D, which illustrate ATR objective 30 for a different input direction for collimated light beam 39. FIG. 3C is the same cross-sectional view of ATR objective 30 shown in FIG. 3A, and FIG. 3D is the same top view of ATR objective 30 as shown in FIG. 3B. In this case, the direction of collimated light beam 39 has changed such that angle 37 is 180 degrees larger than angle 37 shown in FIG. 3B. The point, 38b, at which the collimated light is focused on facet 34 has now moved as shown in FIG. 3C.

An ATR objective according to the present invention is defined to be an optical subsystem having an optical element with a reflection face that internally reflects an input collimated light beam from the reflection face. The reflection face is parallel to the plane of the surface of a specimen being imaged. The collimated input beam is focused to a point on the reflection face at a location that is determined by the angular orientation of the collimated input beam relative to the orientation direction that characterizes an input port to the ATR objective. By changing the angular orientation of the input collimated light beam while maintaining the central ray of the input collimated light beam such that the central ray passes through a pivot point associated with the ATR objective, the point on the reflection face at which the light is focused is changed. In addition, the ATR objective also includes a mask that prevents light from the input beam from striking the reflection face at an angle less than the critical angle for the material from which the optical element is constructed, and thus prevents light from the input beam from directly entering the specimen. Finally, the optical subsystem collects light reflected from the reflection face, collimates that reflected light, and causes that collimated light to exit the ATR objective on a path that is coincident with the path at which the input collimated light beam entered the ATR objective.

The output optical beam is collimated; however, the central portion of that beam is devoid of light, since the light that would have filled that portion of the output optical beam was removed by the mask. To increase the signal-to-noise in the detector that measures the intensity of light in the output optical beam, the detector can be configured as an annular detector to match the cross-section of the output optical beam with a central region that is insensitive to light.

The optical element must be transparent to the MIR light. In one aspect of the invention, the optical element is transparent to light from 3 to 20 microns. In another aspect, the optical element is transparent to light between 5 and 12.5 microns. The later range is sufficient for many chemical identification applications while reducing the cost of the optical element.

In addition, a material with a large index of refraction is preferred to minimize the amount of light that must be blocked to prevent the focused light beam from directly passing into the specimen. in one aspect of the present invention, the preferred optical element is a crystal of a material that is transparent to light in the desired scanning range and which has a planar facet that can be utilized as the face. However, a crystalline material for the optical element is not required. For example, a glass that was transparent to the MIR light could be utilized. In one aspect of the invention, the crystal is chosen from the group consisting of ZnS2, Diamond, ZnS, Ge, Thallium bromide, and Si. Chalcogenide glasses which are transparent to light over a broad range of infrared wavelengths are available commercially.

Figure 4:
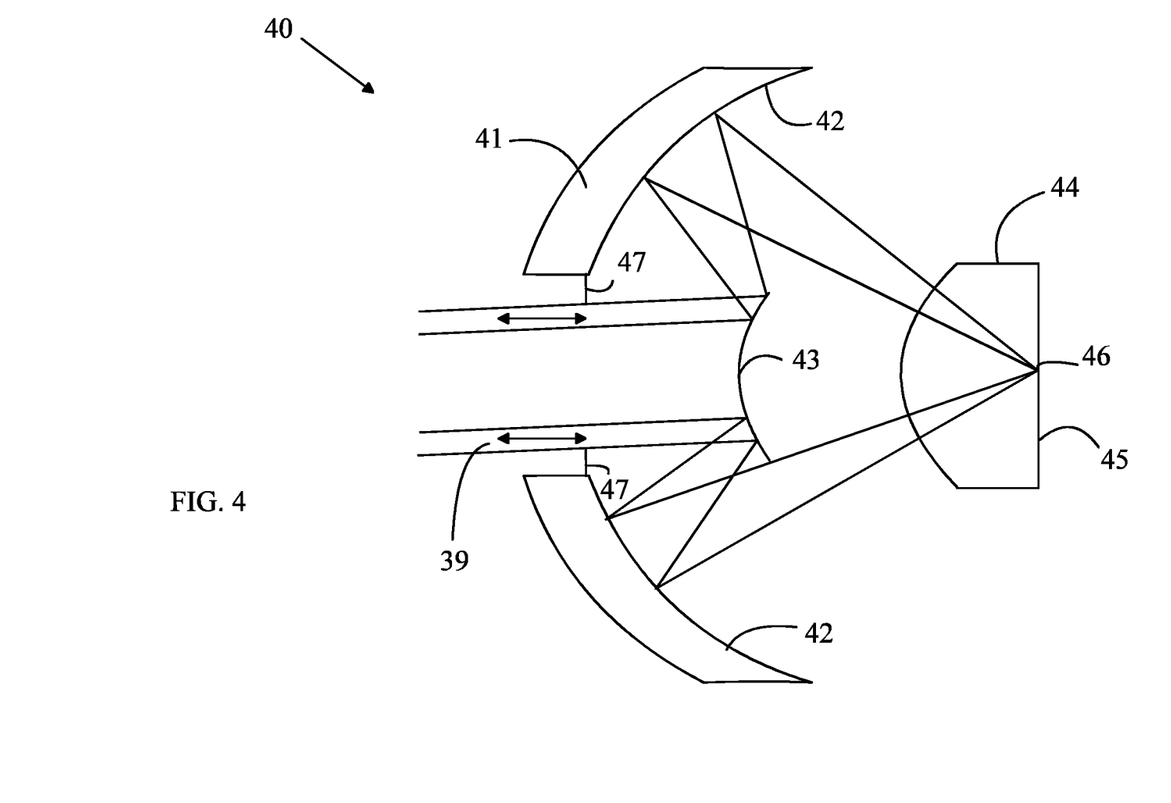
FIG. 4 illustrates an ATR objective that utilizes a reflective optical element to image the input collimated light beam.

The embodiment of an ATR objective shown in FIGS. 3A-3D utilizes a refractive optical component 31 to perform the imaging of the input collimated light beam onto the crystal facet. However, a reflective optical element could also be utilized. Refer now to FIG. 4, which illustrates an ATR objective that utilizes a reflective optical element to image the input collimated light beam. To simplify the drawing, the housing that supports the components discussed below and the specimen have been omitted from the drawing. ATR objective 40 includes a first reflector 41 having a parabolic reflective inner surface 42 that focuses light reflected from a second parabolic reflector 43. Second parabolic reflector 43 also serves the masking function provided by beam blocker 33 described above. Light in the center portion of collimated light beam 39 is blocked from being imaged onto reflective face 45. The area of the second parabolic reflector that does not reflect light that reaches point 46 is preferably coated with a light absorbing material to prevent light reflected by that area from being reflected back in the direction of collimated light beam 39.

The light reflected from parabolic reflective inner surface 42 is focused to a point 46 on reflective face 45 of optical element 44. The light reflected from reflective face 45 is collimated back into a beam that traverses the same path as collimated light beam 39. The location of point 46 depends on the orientation of collimated light beam 39 relative to the aperture of input port 47.

Figure 5:
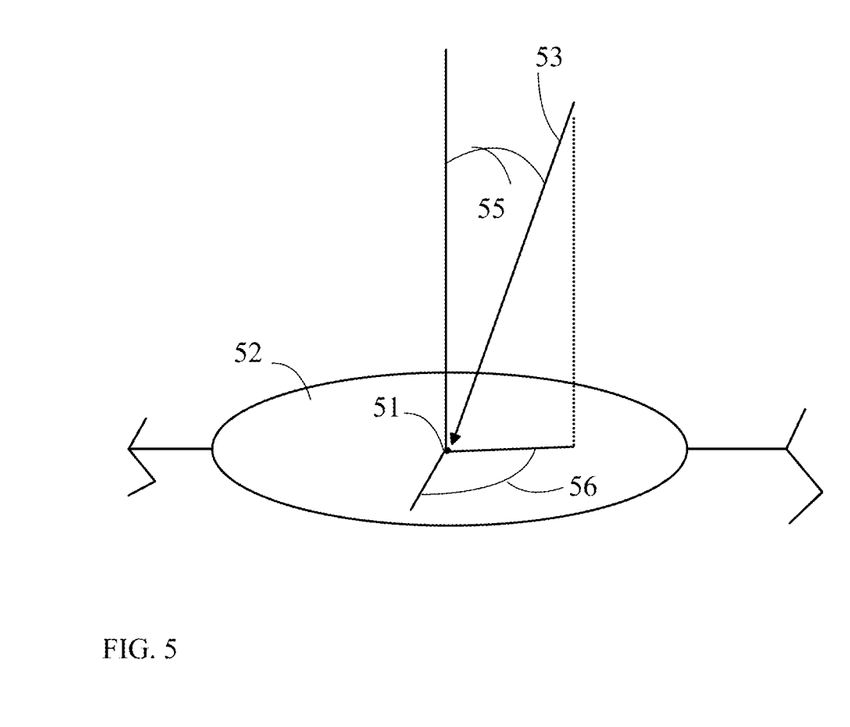
FIG. 5 illustrates the collimated beam motion used to scan the focus point over the reflective face of an ATR objective.

Refer now to FIG. 5, which illustrates the collimated beam motion used to scan the focus point over the reflective face of an ATR objective. In general, an ATR objective has an input port 52 that is characterized by a point 51 at which the central ray 53 of the collimated input beam intersects the plane of the input port. The scanning motion causes the input collimated light beam to change orientation with respect to input port 52 in a manner in which the intersection of central ray 53 with input port 52 maintains central ray 53 such that central ray 53 always passes through point 51. That is, central ray 53 pivots about point 51. The orientation of central ray 53 can be characterized by the angle 55 of central ray 53 with an axis that passes through point 51 and is normal to the input port plane, and by an angle 56 between an axis in the plane of input port 52 and the projection of central ray 53 onto the plane of input port 52. Hence, to cause the focus point on the reflective surface to scan the reflective surface, an optical system that maintains the central ray of the input beam such that it pivots through point 51 but varies angles 55 and 56 is required.

Figure 6:
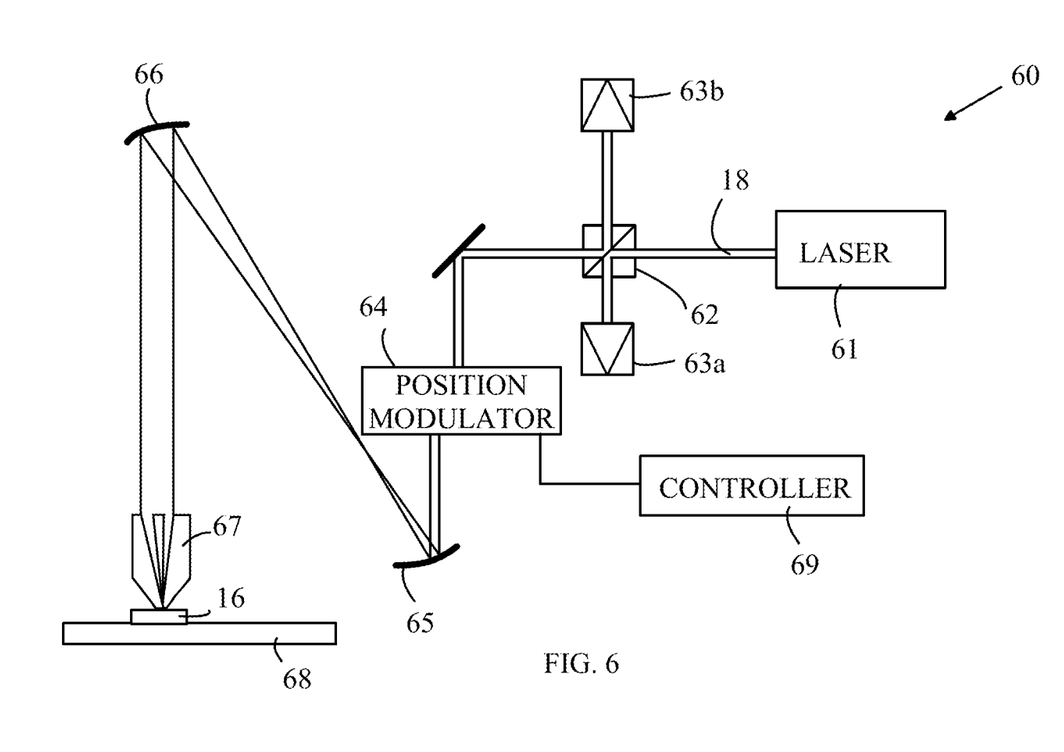

Refer now to FIG. 6, which illustrates a scanning spectrometer according to one embodiment of the present invention. Light from laser 61 is split by beam splitter 62 into two beams. The first beam is directed to detector 63a, which measures the intensity of the laser pulse. The second beam is directed to position modulator 64 which adjusts the point of illumination of the beam on an off-axis parabolic reflector 65. The position of illumination determines the position at which the light from parabolic reflector 65 strikes a second off-axis parabolic reflector 66. Parabolic reflector 66 re-collimates the beam and sets the diameter of the beam to match the input aperture of ATR objective 67. The inclination of the beam entering ATR objective 67 is determined by the point of illumination on parabolic reflector 65. The light reflected back by ATR objective 67 retraces the path of the incoming light and a portion of that light is directed by beam splitter 62 into detector 63b. Controller 69 can then determine the amount of light that was lost in the reflection from ATR objective 67, and hence, determine the amount of light absorbed by specimen 16. To image another small area on specimen 16, controller 69 operates a three axis stage 68.

Figure 7:
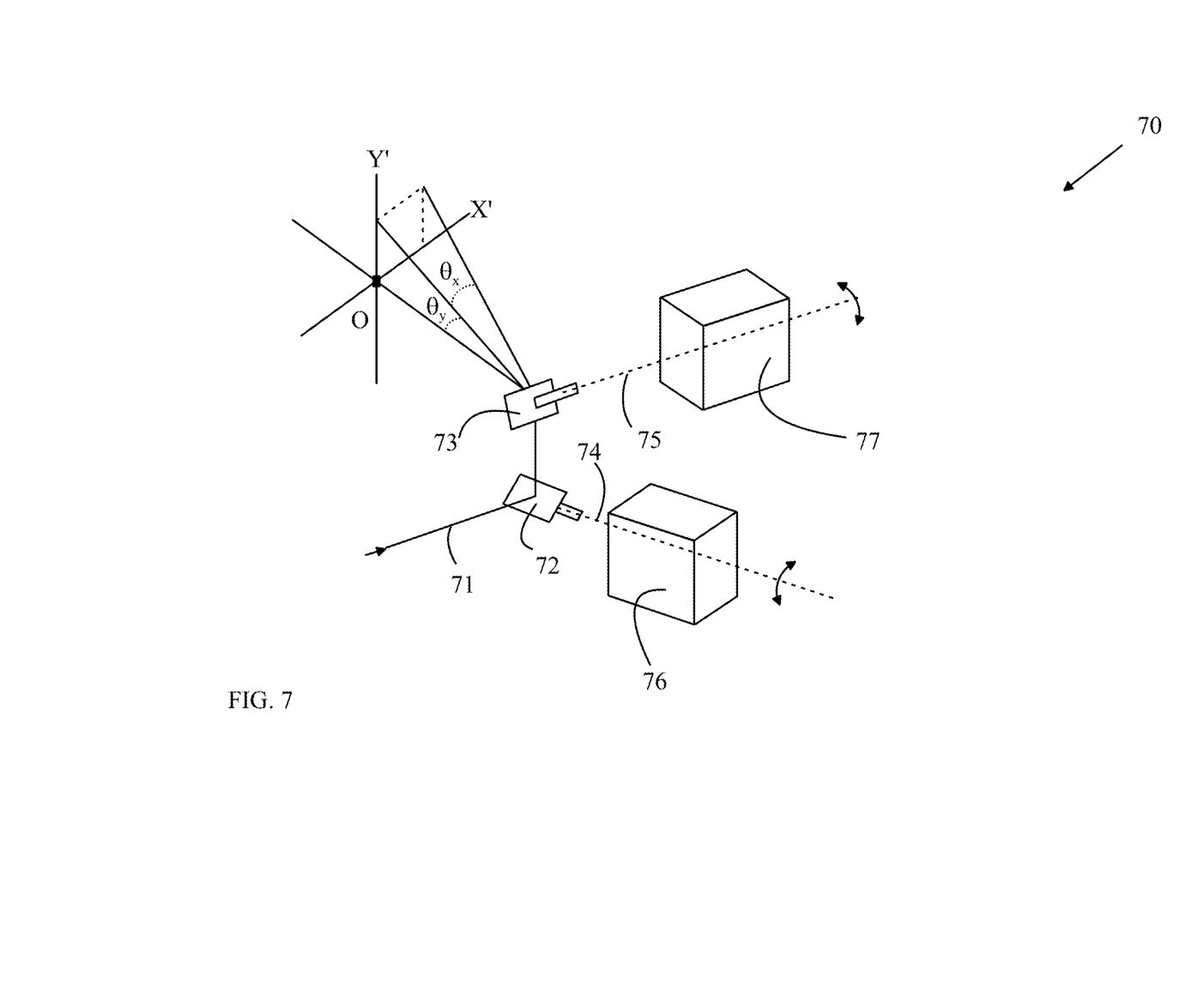
FIG. 7 illustrates a parabolic mirror that utilizes two moving mirrors to cause a collimated light beam to scan in two dimensions.

The above-described embodiments utilize a position to cause a collimated light beam to scan the surface of a parabolic mirror. In one aspect of the invention, a parabolic mirror is constructed from two moving mirrors. Refer now to FIG. 7, which illustrates a parabolic mirror that utilizes two moving minors to cause a collimated light beam to scan in two dimensions. Parabolic mirror 70 includes a first mirror 72 that causes the input beam 71 to scan in a first direction, X', and a second mirror 73 that causes the output of the first mirror to scan in a second direction, Y'. Minors 72 and 73 are caused to rotate about axes 74 and 75, respectively, by actuators 76 and 77, respectively. The actuators can be constructed from galvanic actuators that cause a single mirror to rotate back and forth. The actuators can also be constructed from a polygon scanning mirror that rotates continuously. A MEMS resonator that deflects a single minor with respect to two axes can also be utilized.

Other forms of optical deflectors could also be utilized to cause the beam to scan in two dimensions. For example, acoustic-optical deflectors and electro-optical scanners are also known to the art. In addition, deflectors based on piezo-actuator are known.

Figure 8:
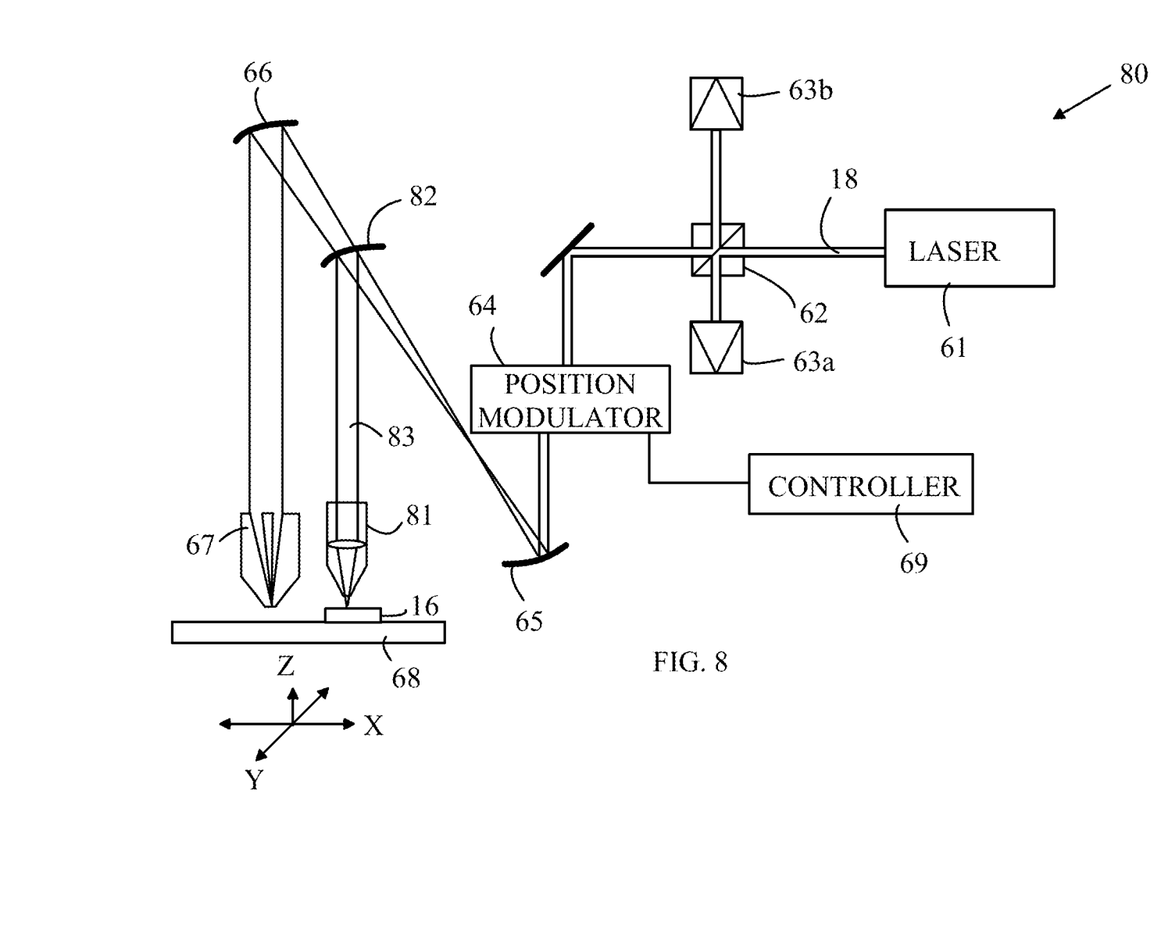
FIG. 8 illustrates one embodiment of a dual mode MIR spectrometer according to the present invention.

It would be advantageous to combine the ability to perform ATR imaging spectroscopy with that of a MIR reflective spectrometer such as imaging system 10 described above with respect to FIG. 1. In one aspect of the invention, the ATR imaging spectrometer 60 shown in FIG. 6 is modified to include a second MIR objective to provide a dual mode scanning spectrometer. Refer now to FIG. 8, which illustrates one embodiment of a dual mode MIR spectrometer according to the present invention. Spectrometer 80 is similar to ATR imaging spectrometer 60 in operation when ATR imaging is utilized, and hence, the components of spectrometer 80 that serve the same functions as components of ATR imaging spectrometer 60 are given the same numerical labels and will not be discussed further here. Spectrometer 80 includes a moveable parabolic mirror 82 which is moved such that moveable parabolic mirror 82 intercepts the light from parabolic reflector 65, collimates that light, and directs the collimated light beam to a MIR objective 81 that focuses the collimated beam on specimen 16. Parabolic reflector 65 is moved via an actuator that is part of parabolic reflector 65 and controlled by controller 69. To simplify the drawing, the actuator and connection to controller 69 have been omitted from the drawing.

When position modulator 64 modulates the position of the light beam striking parabolic reflector 65, the resulting motion causes collimated beam 83 to alter its orientation relative to the input aperture of MIR objective 81, and hence, scan a small area on specimen 16. To scan a larger area, the sample must be repositioned relative to MIR objective 81. The repositioning can be performed by stage 68 or another mechanism that enhances the speed with which MIR objective 81 moves with respect to specimen 16.

To scan a large area on a sample using ATR mode, the large area must be divided into smaller areas that are scanned by positioning the ATR objective over the area of interest and then moving the ATR objective such that it touches the sample surface. This motion requires the stage to be moved in at least two directions between scan areas. In contrast, when scanning in the MIR reflective mode, the sample does not have to be in contact with the objective. Hence, when moving from one small area to the next, the sample and stage need only move in one direction with respect to one another. The mass of the objective is much less than the mass of the stage, and hence, it is advantageous to move the objective in one direction rather than moving the stage in that direction.

Figure 9:
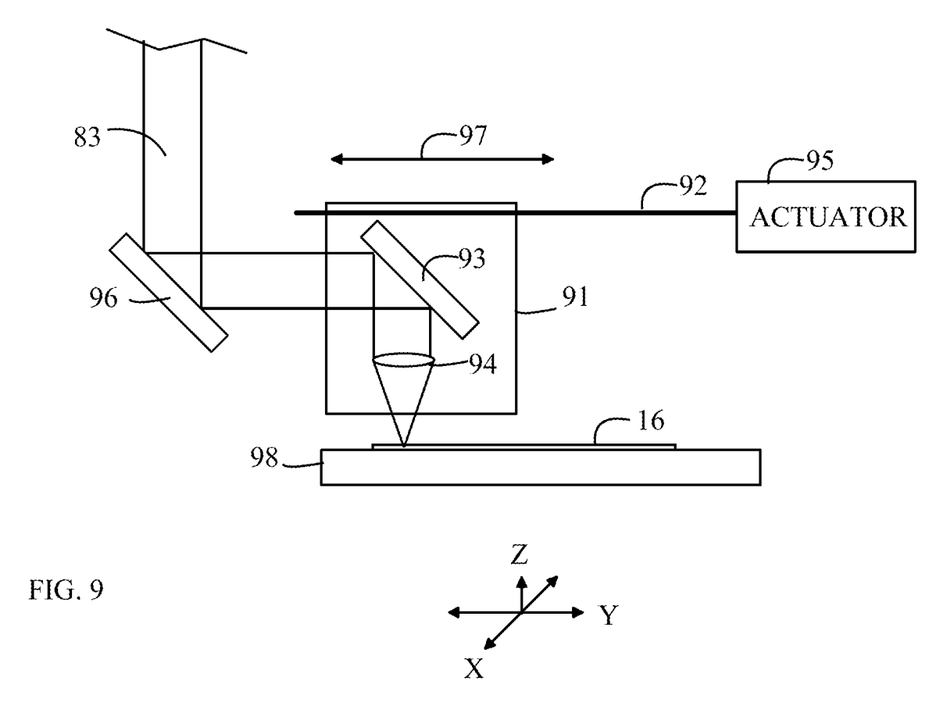
FIG. 9 illustrates a scanning reflective objective that can be used in the spectrometer shown in FIG. 8.

Refer now to FIG. 9, which illustrates a scanning reflective objective that can be used in the spectrometer shown in FIG. 8. Objective 91 is mounted on a rail 92 that moves in the Y-direction. Objective 91 includes a mirror 93 that directs a collimated beam of light to a optical system 94 that focuses that light to a point on specimen 16. To simplify the drawing a single lens is shown in the drawing; however, it is to be understood that the optical system can involve a number of lens elements. The mass of objective 91 is much smaller than that of stage 98, and hence, stage 98 can be moved at a much faster speed. Rail 92 includes a linear actuator 95 that couples to objective 91 to provide the required motion 97. A mirror 96 moves collimated beam 83 shown in FIG. 8 to objective 91. In one aspect of the invention, position modulator 64 shown in FIG. 8 can be operative during the scanning with objective 91 to provide a small scanning amplitude in the X-direction while objective 91 is moved in the Y-direction. This aspect of the invention allows the spectrometer to image in a spatial band, and hence, reduce the number of Y-positions that must be provided by stage 98 to scan a given area.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. An attenuated total reflection (ATR) objective comprising:
   a first optical element comprising a planar face;
   an input port adapted to receive an input collimated light beam characterized by a central ray, said input port being characterized by a pivot point through which said central ray passes;

a mask that divides said input collimated light beam of light into first and second portions, said mask preventing light in said first portion from reaching said planar face; and a second optical element that focuses said second portion on a point on said planar face such that substantially all of said second portion is reflected from said planar face, said second optical element collecting light reflected from said planar face and collimating said collected light into an output collimated light beam that leaves said input port, said output collimated light beam a central ray coincident with said central ray of said input collimated light beam.

2. The ATR objective of claim 1 wherein said mask absorbs light in said first portion.

3. The ATR objective of claim 1 wherein said first optical element s transparent to light having a wavelength between 3 and 20 microns.

4. The ATR objective of claim 1 wherein said first optical element is transparent to light having a wavelength between 5 and 12.5microns.

5. The ATR objective f claim 1 wherein said first optical element comprises a crystalline material and said planar face is a facet of a crystal of said crystalline material.

6. The ATR objective of claim 1 wherein said first optical element comprises a glass that is transparent to light having a wavelength between 3 and 20 microns.

7. The ATR objective of claim 1 wherein said first optical element comprises a glass that is transparent to light having a wavelength between 5 and 12.5 microns.

8. The ATR objective of claim 1 wherein said second optical element is a refractive element.

9. The ATR objective of claim 1 wherein said second optical element is a reflective element.

10. The ATR objective of claim 1 wherein said input port is characterized by a direction that passes through said pivot point and wherein said point on said planar face depends on an orientation of said central ray of said input collimated light beam relative to said direction.

11. A scanner comprising:
a light source that generates a first collimated light beam;
an ATR objective comprising:
a first optical element comprising a planar face, said planar face being characterized by a critical angle;
an input port adapted to receive a first input collimated light beam characterized by a central ray, said input port being characterized by a pivot point through which said central ray passes and an orientation direction that passes through said pivot point; and
a second optical element that focuses a portion of said first input collimated light beam to a point on said planar face such that substantially all of said portion is reflected by said planar face and no portion of said input collimated light beam strikes said planar face at an angle less than said critical angle, said second optical element generating a first output collimated light beam from light reflected from said planar face, said first output collimated light beam being characterized by a central ray that is coincident with said central ray of said first input collimated light beam;
a first detector that measures an intensity of light in said first output collimated light beam; and
a light beam converter that receives said first collimated light beam and generates said first input collimated light beam therefrom in response to an orientation signal that determines an orientation between said orientation direction and said central ray of said input collimated light beam.

12. The scanner of claim 11 further comprising a second detector that measures an intensity of light in said first collimated light beam.

13. The scanner of claim 11 further comprising a controller that generates said orientation signal and causes said light beam converter to sequence through a predetermined set of different orientations between said orientation direction and said central ray of said input collimated light beam.

14. The scanner of claim 11 wherein said light beam converter comprises:
first and second parabolic reflectors; and
a position modulator that receives said first collimated light beam and deflects that light beam to a point on said first parabolic reflector, said point being determined by said orientation signal,
said second parabolic reflector being positioned to receive light reflected from said first parabolic reflector and collimating said received light to generate said first input collimated light beam.

15. The scanner of claim 14 further comprising:
a reflective objective comprising
an input port configured to receive a second input collimated light beam characterized by a central ray;
an optical elementthat focuses said second input collimated light beam to a spot at a predetermined point, said optical element receiving light reflected from said predetermined point and forming a second output collimated light beam therefrom, said second output collimated light beam being characterized by a central ray that is coincident with said central ray of said second input collimated light beam; and
a third parabolic reflector that intercepts light reflected from said first parabolic reflector and generates said second input collimated light beam therefrom when said third parabolic reflector is in a first position and that does not intercept light from said first parabolic reflector when said third parabolic reflector is in a second position, said first and second positions of said third parabolic reflector being determined by an actuator that is responsive to a mode signal.

16. The scanner of claim 15 further comprising an actuator that moves said reflective objective in relationship to a specimen stage such that said spot moves in a line parallel to said specimen stage.

17. The scanner of claim 16 wherein said controller causes said position modulator to move said point on said first parabolic reflector such that said spot moves in a direction orthogonal to said line.

* * * * *

UNITED STATES PATENT AND TRADEMARK OFFICE
CERTIFICATE OF CORRECTION

PATENT NO. : 9,863,877 B2  
APPLICATION NO. : 14/863341  
DATED : January 9, 2018  
INVENTOR(S) : Charles Hoke et al.

Page 1 of 1

It is certified that error appears in the above-identified patent and that said Letters Patent is hereby corrected as shown below:

On the Title Page

In item (57), in Column 2, in "Abstract", Line 11, delete "thce" and insert -- face --, therefor.

In the Specification

In Column 1, Line 44, delete "reflected." and insert -- reflected --, therefor.

In Column 2, Line 15, delete "minor" and insert -- mirror --, therefor.

In Column 6, Line 15, delete "in" and insert -- In --, therefor.

In Column 7, Line 32, delete "minors" and insert -- mirrors --, therefor.

In Column 7, Line 36, delete "Minors" and insert -- Mirrors --, therefor.

In Column 7, Line 43, delete "minor" and insert -- mirror --, therefor.

In the Claims

In Column 9, Line 18, in Claim 3, delete "s" and insert -- is --, therefor.

In Column 9, Line 22, in Claim 4, delete "12.5microns." and insert -- 12.5 microns. --, therefor.

In Column 9, Line 23, in Claim 5, delete "f" and insert -- of --, therefor.

In Column 10, Line 33, in Claim 15, delete "elementthat" and insert -- element that --, therefor.

Signed and Sealed this  
Thirty-first Day of July, 2018

Andrei Iancu  
*Director of the United States Patent and Trademark Office*